(12) United States Patent
Freeman

(10) Patent No.: US 6,201,992 B1
(45) Date of Patent: Mar. 13, 2001

(54) DEFIBRILLATOR INTERFACE CAPABLE OF GENERATING VIDEO IMAGES

(75) Inventor: Curtis Freeman, Windham, NH (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/283,564

(22) Filed: Apr. 1, 1999

(51) Int. Cl.[7] ........................................ A61N 1/39
(52) U.S. Cl. ........................................... 607/5
(58) Field of Search ................ 607/1, 5; 434/262, 434/265; 600/510

(56) References Cited

U.S. PATENT DOCUMENTS

| | | | |
|---|---|---|---|
| 4,898,179 | * 2/1990 | Sirota | 600/528 |
| 5,285,792 | 2/1994 | Sjoquist et al. | 128/697 |
| 5,593,426 | 1/1997 | Morgan et al. | 607/5 |
| 5,792,190 | 8/1998 | Olson et al. | 607/5 |
| 5,797,969 | 8/1998 | Olson et al. | 607/5 |
| 5,913,685 | * 6/1999 | Hutchins | 434/265 |

* cited by examiner

Primary Examiner—W. Kamm

(57) ABSTRACT

A defibrillator includes circuitry configured to produce a defibrillatory shock and an audio/video output unit having a database of video image information stored in a memory, a video display, and a video formulation unit coupled to the memory and configured to retrieve video information from the database of video image information and present corresponding information to the video display for display. The video information may include still images, animated images, motion images or a combination of textual information and at least one of still images, animated images and motion images. The audio/video output unit may be configured to receive inputs relating to user inputs, patient signals and device inputs, and to provide video instructions, and optionally audio or textual instructions, relating to operation of the defibrillator based on the current operational state of the defibrillator.

20 Claims, 4 Drawing Sheets

DEFIBRILLATOR INTERFACE CAPABLE OF GENERATING VIDEO IMAGES

BACKGROUND OF THE INVENTION

1. Field of the Invention

The present invention relates generally to defibrillators and, more particularly, to a portable external defibrillator having user interface prompts to assist an operator of a defibrillator.

2. Related Art

Sudden cardiac arrest is a disruption of the heart's functioning that causes a lack of blood flow to vital organs. In a majority of instances, sudden cardiac arrest is manifested as an abnormal or chaotic heart rhythm, called fibrillation. These instances are generally identifiable by the victim's immediate loss of pulse, loss of consciousness and a cessation of breathing.

Sudden cardiac arrest has been attributed to over 350,000 deaths each year in the United States, making it one of the country's leading medical emergencies. World-wide, sudden cardiac arrest has been attributed to a much larger number of deaths each year. Unless immediate medical intervention is initiated, sudden cardiac arrest can lead to death within a matter of minutes.

There are four critical components of medical treatment that must be administered to a victim of sudden cardiac arrest: (1) early access to emergency care; (2) early cardiopulmonary resuscitation to keep the blood oxygenated and flowing to the victim's brain and other vital organs; (3) early defibrillation (the application of an electrical shock to the heart) to restore the heart's regular rhythm; and (4) early access to advanced medical care. When a person is experiencing sudden cardiac arrest, the electrical activity within the heart becomes chaotic. An electric shock from a defibrillator can reorganize the electrical impulses to allow coordinated pumping action to resume. To administer this shock, special pads from a machine called a defibrillator are placed on the victim's chest, and an electric shock is sent through the victim's body from one pad to another. As used herein, the term "pads" will include both pads and paddles.

If prompt cardiopulmonary resuscitation is followed by defibrillation within about four minutes, the victim's chances of surviving sudden cardiac arrest can approach or exceed fifty percent. Prompt administration of defibrillation within the first critical minutes is considered one of the most important components of emergency medical treatment for preventing death from sudden cardiac arrest.

Since prompt defibrillation is critical to survival, portable defibrillators have been developed that can be carried to the victim's location to defibrillate the victim prior to reaching a hospital. Initially, portable defibrillators were manual devices that could be used safely only by persons having a high level of medical training. Defibrillators with advanced decision making functions, called automatic external defibrillators or semiautomatic external defibrillators, have since been developed that can be used safely by emergency personnel with less advanced medical training. The term "automatic external defibrillator" will be used herein to include both automatic external defibrillators and semiautomatic external defibrillators.

Today, portable defibrillators are easy to operate and have built-in computers that guide users through the defibrillation procedure. These automatic external defibrillators can assess the patient's heart rhythm to determine whether defibrillation is necessary and, if defibrillation is required, will signal the operator to shock the patient. If a shock is not required, the defibrillator will not allow a shock to be administered to the patient.

Persons operating under the intense pressure of an emergency medical situation may forget a substantial amount of their training or may fail to understand the instructions being provided by the defibrillator. In rural areas, operators of defibrillators tend to have a low frequency of exposure to sudden cardiac arrest situations. Additional prompts can help them to remember their training. Also, there is a trend to place portable defibrillators in areas of hospitals not generally staffed with emergency personnel and in other public areas where difficult to reach arrhythmic patients are likely to be encountered, such as airplanes, airports, cruise liners, casinos, sports arenas and other populous facilities that are difficult or time consuming to access. An operator in this situation may have little or no training on operation of the particular defibrillator thus compounding the confusion and stress associated with resuscitating the victim.

To alleviate these sources of operation error, various instructional mechanisms have been developed to enable the defibrillator to prompt the operator during operation of the defibrillator in real time. One conventional technique for providing prompts has been to provide audio prompts in connection with text prompts displayed on the defibrillator display. Unfortunately, the limited amount of space available for displays and time constraints prevent the operator from reading a detailed description of the next action to be taken. Accordingly, it would be advantageous to have a defibrillator with an user interface capable of providing additional assistance to operators during deployment and operation of the defibrillator. Further, it would be advantageous to have a defibrillator that could start to neutralize adverse effects inexperience may have on operation of the defibrillator.

SUMMARY OF THE INVENTION

The present invention is a portable external defibrillator having an user interface capable of assisting operators during deployment and operation of the defibrillator, and that can start to neutralize adverse effects inexperience may have on operation of the defibrillator. In one aspect, the invention relates to an external defibrillator having a video driver for providing additional context through video prompts in response to current operational conditions of the defibrillator, to assist in guiding the operator through the process of defibrillating a victim.

In one embodiment, a defibrillator includes circuitry configured to produce a defibrillatory shock and an audio/video output unit. In this embodiment, the audio/video output unit includes a database of video image information stored in a memory, a video display, and a video formulation unit coupled to the memory and configured to retrieve video information from the database of video image information and present corresponding information to the video display for display. The video information may include still images, animated images, motion images or a combination of textual information and at least one of still images, animated images and motion images. The video information may be stored in the database of video image information as bit map files.

The audio/video output unit may include a controller configured to receive signals indicative of a current operating state of the defibrillator, and the video formulation unit may be configured to retrieve video information from the database of video information corresponding to the current operating state of the defibrillator. An audio speaker may be provided and the video formulation unit may be configured to receive audio information from the database of video information and correlate the video information to be displayed with the received audio information to be output by the audio speaker.

The audio/video output unit may also include an output generator configured to receive the video image information and determine a duration and sequencing of images for display by the video display, and an instruction generator having a memory configured to contain instructions relating to operation of the audio/video output unit, the instruction generator being configured to receive signals indicative of the operating state of the defibrillator and to return at least one operational instruction derived from information contained in the memory.

In another embodiment, a defibrillator includes circuitry configured to deliver a defibrillatory shock, and an audio/video output unit. In this embodiment, the audio/video output unit is configured to receive inputs relating to a current operational state of the circuitry configured to deliver the defibrillatory shock, and to provide audio and video instructions, and optionally textual instructions, relating to operation of the defibrillator.

In yet another embodiment, a method of instructing an operator of a defibrillator during defibrillation of a victim of sudden cardiac arrest, includes determining a current operating state of the defibrillator, optionally by sensing user inputs, patient signals or device inputs, and providing video instructions to the operator related to the current operating state of the defibrillator. In this method, audio or textual instructions may be provided as well as video instructions.

BRIEF DESCRIPTION OF THE DRAWINGS

This invention is pointed out with particularity in the appended claims. The above and further advantages of this invention may be better understood by referring to the following description when taken in conjunction with the accompanying drawings, in which:

DETAILED DESCRIPTION

The present invention is an external defibrillator having an audio/video output unit that provides video images and, optionally, audio prompts during operation of the defibrillator. As used herein, the term "video image" will be used to encompass both still graphical images, sequences of images, motion images, animations, and other types of video displays, but not purely textual images, that is, a video image may include text, but will not be formed entirely of text. The video images may be provided in response to current operational conditions of the defibrillator and are tailored to assist in guiding the operator through the process of defibrillating a person experiencing sudden cardiac arrest.

Simple graphics or animations within limited display space can offer more information and convey an idea more quickly and clearly than simple text. Additionally, video information may convey additional context and information that is difficult to convey using succinct audio or textual prompts, such as the location of placement of pads on the victim, the proper positioning of the operator hands during CPR, etc. It is believed that images can then help a user more quickly and accurately understand what needs to be done in a highly stressful situation, such as when resuscitating a victim of sudden cardiac arrest, and thus reduce the frequency with which mistakes will occur.

Figure 1:
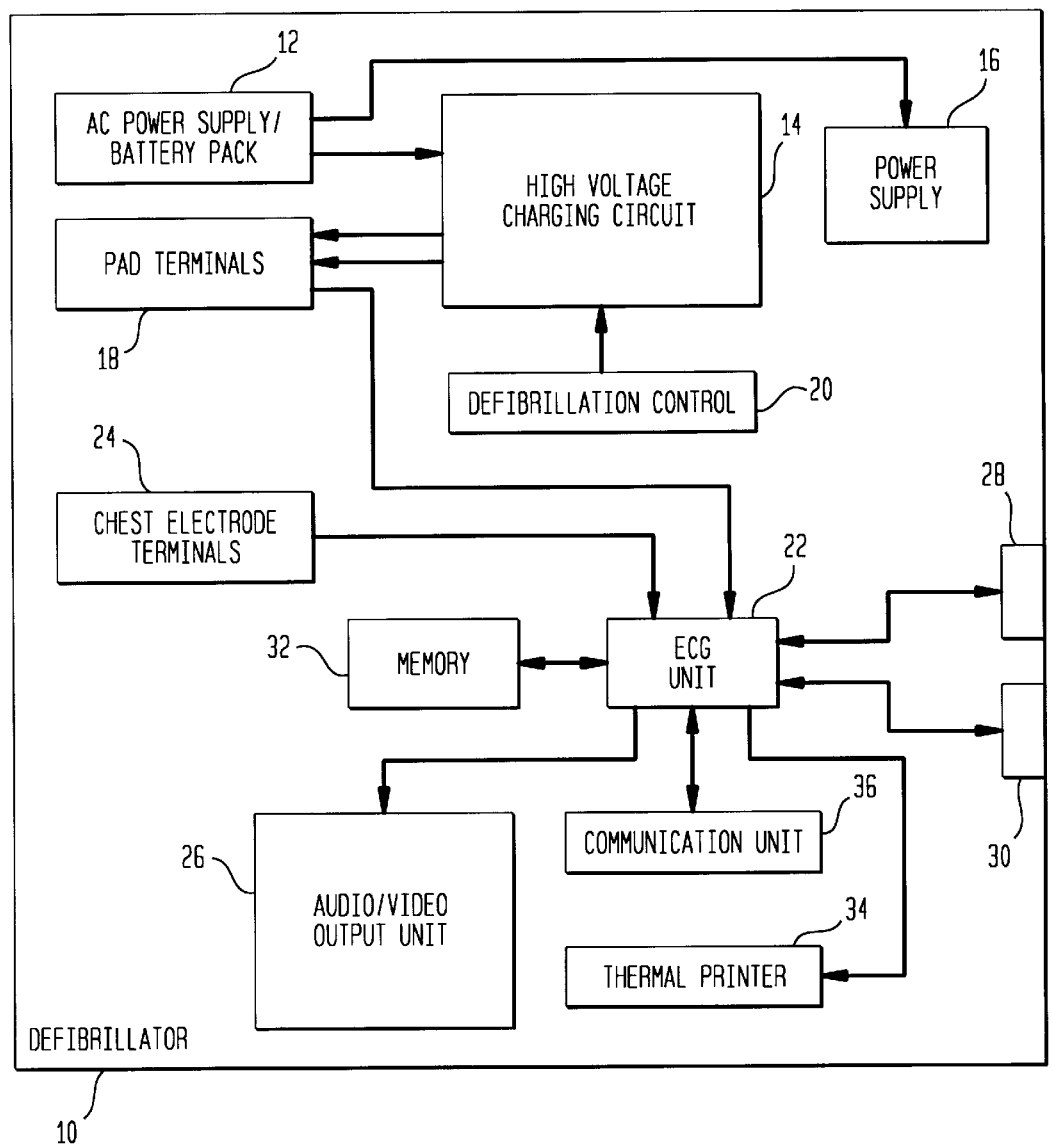
FIG. 1 is a functional block diagram of a defibrillator according to one embodiment of this invention.

With reference now to the figures and in particular with reference to FIG. 1, there is illustrated a block diagram of a defibrillator in accordance with one embodiment of the present invention. In the illustrated embodiment, the defibrillator 10 includes a rechargeable battery pack 12 which supplies power to defibrillator 10. The invention is not limited in this respect, and includes a defibrillator powered by any suitable power supply, such as a rechargeable battery pack, disposable battery pack, AC power supply, etc. The illustrated defibrillator 10, as a battery-powered device, is highly portable and therefore suitable for pre-hospital (emergency) use. Battery pack 12 preferably includes one or more batteries, such as nickel-cadmium (NiCd), lithium, or sealed lead/acid batteries, capable of providing power for several hours of operation. As illustrated, battery pack 12 is electrically coupled to high voltage charging circuit 14 and supplies charge to a large capacitor contained within high voltage charging circuit 14 utilized to store a large charge sufficient to defibrillate an arrhythmic patient. Battery pack 12 is further electrically coupled to power supply 16, which supplies power to the control and monitoring circuitry within defibrillator 10. High voltage charging circuit 14 is electrically connected to a pair of pads utilized to deliver a defibrillating shock to an arrhythmic patient via a pair of pad terminals 18. The delivery of the defibrillating shock to the arrhythmic patient by a high voltage charging circuit 14 is controlled by defibrillation control 20.

Still referring to FIG. 1, defibrillator 10 further includes electrocardiogram (ECG) unit 22, which controls the monitoring functions of defibrillator 10. From the following description of ECG unit 22, those skilled in the art will appreciate that ECG unit 22 may be implemented utilizing a conventional microprocessor and support circuitry, or alternatively, an application-specific integrated circuit (ASIC). ECG unit 22 receives ECG data from a patient through chest electrodes connected to the defibrillator 10 via chest electrode terminals 24. The chest electrodes are preferably coated with a conductive gel to establish a good electrical contact with the patient. Optionally, as is well known, the ECG data can be acquired through the pads via the pad terminals 18. The ECG data received from the patient is temporarily buffered in an ECG data buffer within ECG unit 22 and may be displayed in real-time to the operator of defibrillator 10 via audio/video output unit 26. The ECG data is preferably displayed in the form of a conventional ECG waveform trace, and may be displayed in conjunction with additional information extracted from the ECG data, such as the patient's instantaneous pulse rate.

A memory 32 is provided to store ECG data and other data of interest to medical and legal personnel reviewing the operation of the defibrillator after its use. To facilitate access to stored data, memory 32 may include a removable and portable data storage device, such as a PCMCIA (Personal Computer Memory Card International Association) memory card; or may be implemented as a nonremovable memory device.

ECG unit 22 is further coupled to user controls 28, 30 that enables the user to interact with the defibrillator 10. Control 28, for example, may be configured as a "mark" button 28 which is depressed by an operator to store ECG data of interest within memory 32. During treatment of a patient, the operator typically utilizes mark button 28 to record segments of ECG data sensed before and after the administration of drugs, the delivery of shocks, and other significant treatment events.

The collection of ECG data segments stored in memory 32 by the operator during treatment of a patient, known as a "code" summary, can be printed by the operator of defibrillator 10 on thermal printer 34 by depressing review button 30. Alternatively, the ECG unit 22 can store all of the patient's ECG data sensed during treatment within memory 32 in conjunction with a list of marked events for later use. The ECG unit 22 may be configured to automatically mark events preselected by the operator, such as the delivery of shocks.

In addition, defibrillator 10 preferably includes a communication unit 36, such as an infrared serial port, modem or other type of data communication device, to enable the content of memory 32 or selected operations of the ECG unit 22 to be downloaded directly to a computer for supervision, review and/or analysis.

ECG unit 22 is further coupled to audio/video output unit 26. Audio/video output unit 26 is configured to provide audio and video outputs to the defibrillator operator. Optionally, the audio/video output unit 26 may also be configured as an audio and/or video input unit to receive audio input via a microphone, or video input via, for example, a video camera, digitize the audio or video data if not already in digital form, and store the digital information in memory 32 via ECG unit 22. As will be appreciated by those skilled in the art, the audio and video data to be displayed and/or received can be compressed during storage utilizing any of a number of wellknown data compression algorithms in order to minimize the amount of space in memory 32 required to store the data.

Figure 2:
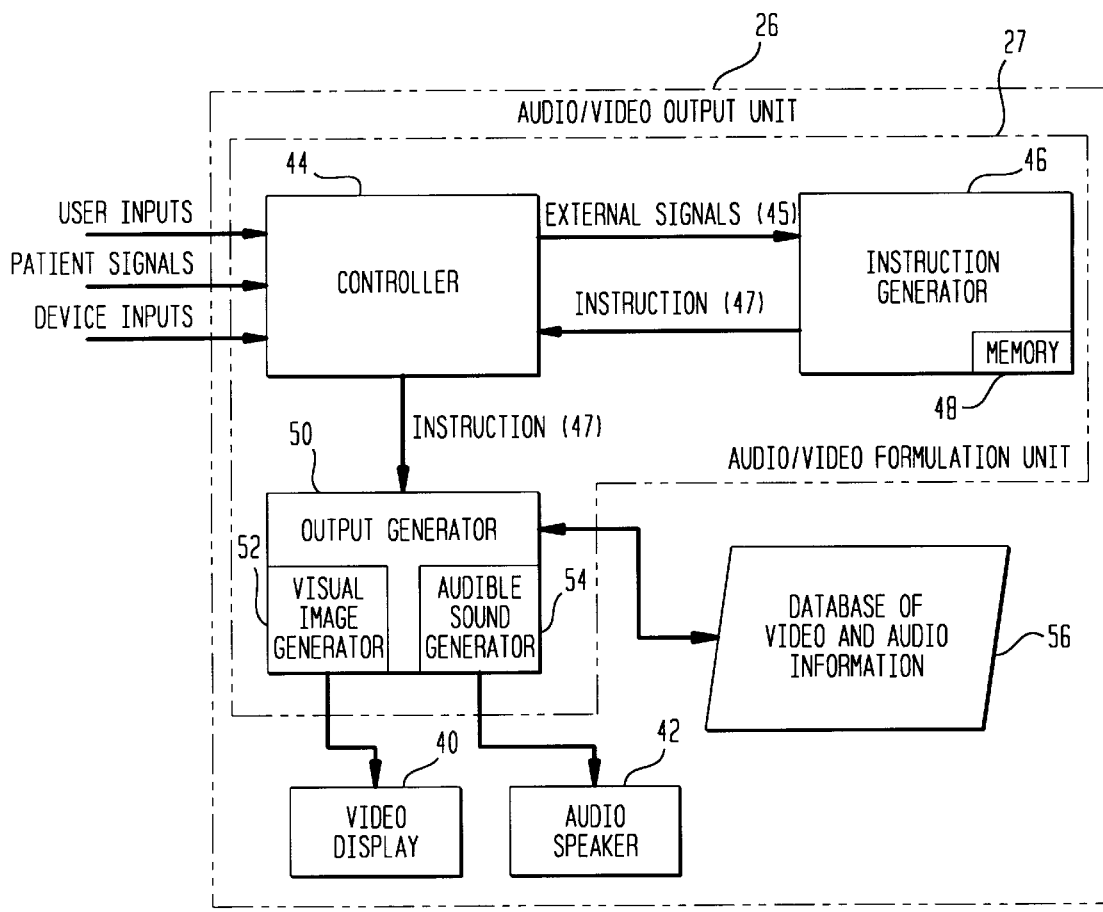
FIG. 2 is a functional block diagram of an audio/video output unit for use in the defibrillator of FIG. 1.
Figure 3A:
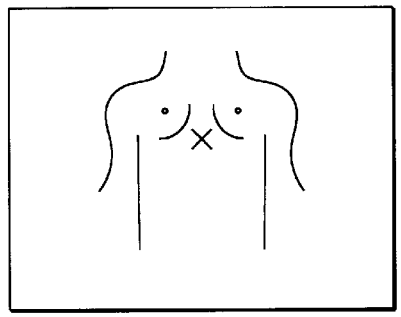
FIGS. 3a–3d are a first sequence of images to be displayed by the audio/video output unit of FIG. 2.
Figure 4A:
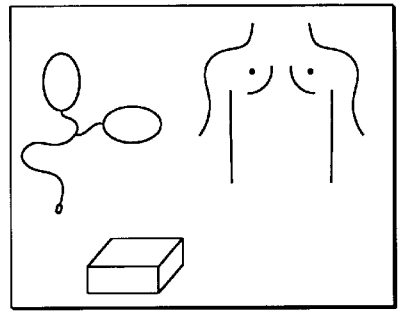
FIGS. 4a–4d are a second sequence of images to be displayed by the audio/video output unit of FIG. 2.
Figure 3B:
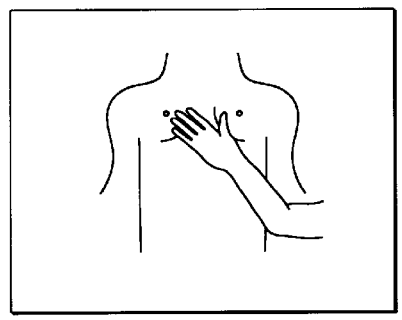
Figure 4B:
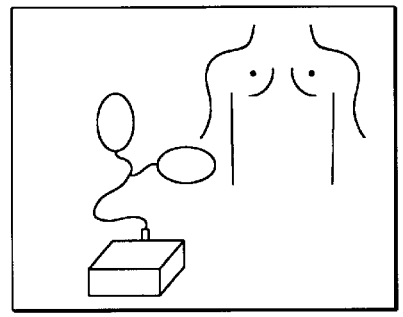
Figure 3C:
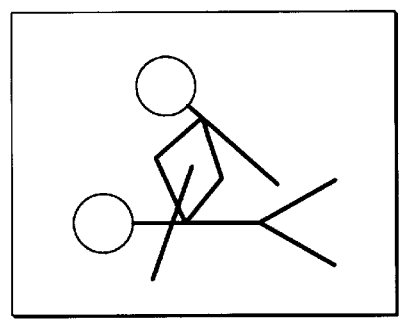
Figure 4C:
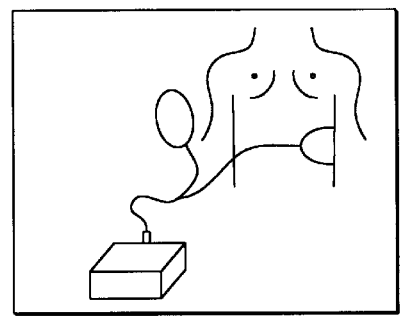
Figure 3D:
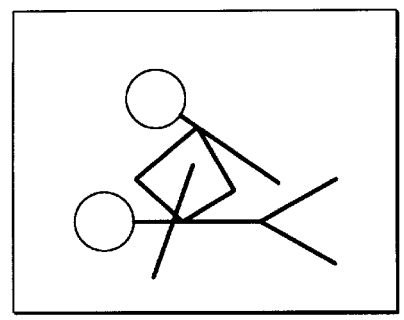
Figure 4D:
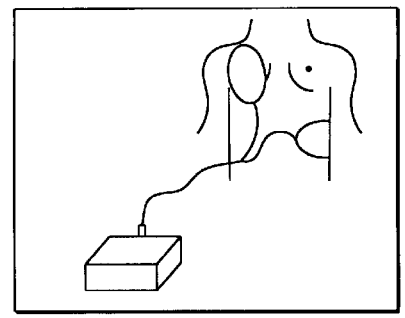

FIG. 2 illustrates one exemplary embodiment of audio/video output unit 26. In this exemplary embodiment, both audio and video instructions are provided. Optionally, the portion relating to provision of audio instructions could be eliminated if desired.

As shown in FIG. 2, the audio/video output unit 26 includes an audio/video formulation unit 27 configured to formulate video and, optionally, audio instructions for display by the defibrillator 10, a database of video and audio information 56, a video display 40 configured to display video images, and an audio speaker 42 for broadcasting information to the operator of the defibrillator. Optionally, the database 56 may be contained within memory 32. Because the video display 40 is configured to display video images, the defibrillator can augment or replace simple textual instructions and audible instructions to convey significant additional information. This additional information may help the operator to defibrillate the person experiencing sudden cardiac arrest and may reduce the occurrence of improper operation of the defibrillator.

The video display 40 may be any device having the ability to generate and display a video image, such as a liquid crystal display (LCD), a cathode ray tube (CRT) display or any other such device. Likewise, the audio speaker 42 may be any conventionally available speaker capable of generating audible signals from digital or analog information.

The video images to be displayed on the video display 40 may be still images that are maintained on the screen for a relatively long period of time, or may be sequential images displayed in relatively rapid succession to provide the illusion of motion to the user. The images are preferably, but not necessarily, timed to coincide with the audible instructions generated by audio speaker 47 and may also be accompanied by textual instructions and/or ECG data also displayed on the video display 40. Exemplary sequences of video images are shown in FIGS. 3A–3D and 4A–4D, as discussed more fully below.

The audio/video formulation unit 27 contains components configured to receive information relating to the operational state of the defibrillator and generate video images to be displayed on the video display 40. Implementation of an audio/video formulation unit and video database, and synchronization of video images with textual or audio prompts is within the scope of a person of ordinary skill in the art. From the following description of audio/video output unit 26 and audio/video formulation unit 27, those skilled in the art will appreciate that audio/video output unit 26 and audio/video formulation unit 27 may be implemented utilizing a conventional microprocessor and support circuitry, or alternatively, an application-specific integrated circuit (ASIC).

The audio/video output unit 26 includes a controller 44 that receives inputs relating to the operational status of the defibrillator. In FIG. 2, these inputs are labeled "User Inputs," "Patient Signals" and "Device Inputs." In one exemplary embodiment, the audio/video output unit 26 may receive information from the user via the "User Inputs" such as indications that the operator has depressed one or more buttons, e.g. button 28 or 30; may receive information from the patient via the "Patient Signals", such as the instantaneous heart rate, ECG or SpO2 data; and may receive information relating to the operational state of the defibrillator for the other components if the defibrillator itself via "Device Inputs," such as impedance data, internal voltage data, component status data, etc. Other inputs could be provided to the controller 44 as well. The signals received by the controller 44 from circuitry external to the audio/video output unit 26 will be termed "external signals" herein.

The controller 44 may transmit a subset of the external signals to the video display 40 for display to the user. Examples of such external signals include ECG data, instantaneous heart rate information, mark indications, and any other information that may be desirably displayed to the operator. The controller 44 also conveys external signals 45 containing information from at least a subset of the external signals to an instruction generator 46.

The instruction generator 46 receives information relating to the operational state of the defibrillator from the controller 44 and formulates a response to the current state of the device. This information may include any of the information contained in the external signals, i.e., information from the user (such as button pushes or other responses), patient signals (such as heart rate or ECG data), or information from the device itself (such as impedance data, internal voltages, etc.). The instruction generator 46 includes an instruction memory 48, such as a random access memory (RAM) or a read only memory (ROM), containing software code used to generate system responses. The instruction generator 46 may also include a gate array or other control logic.

The response (instruction 47) determined by the instruction generator 46 is communicated via the controller 44 to the output generator 50, which in this embodiment includes a visual image generator 52 and an audible sound generator 54. The output generator 50 queries the database 56 to determine the proper set of outputs and retrieves the video and audio information to be displayed from the database 56. The database 56 may be contained within the audio/video output unit 26 or may be contained in memory 32. The output generator 50 also retrieves presentation information, such as the duration of any output and how to sequence or synchronize the various outputs. This retrieved information is passed to the visual image generator 52 and audible sound generator 54 which format and send signals to the video display 40 and audio speaker 42, respectively.

In this manner, the audio/video output unit 26 processes receives information using known techniques, determines the operational state of the defibrillator and determines commands to output in visual and audio form. Depending on the operational state of the defibrillator and condition of the patient, the display controller 44 will recall the appropriate images from the database of video and audio information 56 and cause images to be displayed on the video display 40. Preferably, the displayed images are timed to correlate with broadcasted audio instructions and/or displayed textual instructions. However, as long as video images are displayed, audio and textual prompts need not be provided.

Graphical images providing step-by-step instructions or status information thus can be displayed in lieu of or in addition to simple text to augment the audio prompts to guide the user in the operation of the device. Several examples of sequenced images that may be displayed are illustrated in FIGS. 3A–3D and 4A–4D. Additional or different images may be used depending on the particular timing of display of the images, the capabilities of the display, and the proficiencies of the artist's rendering, such as those sequences of images shown in FIGS. 6–10.

A first example of video images that may be displayed by the video display 40 are shown in FIGS. 3A–3D. In this example, the operator is provided instruction on performing CPR. The audio prompt may be saying "Check the patient's airway. Check pulse. Check breathing. If necessary, perform CPR." Images such as those illustrated in FIGS. 3A–3D simultaneously or subsequently provided could help the user recall CPR hand placement, and animation of the last two images could illustrate chest compressions occurring at the recommended frequency of 90 beats per minute.

Another example of images that may be displayed are illustrated in FIGS. 4A–4D. These images may be used to augment an audio prompt such as "Apply pads to the patient's bare chest. Plug in the pad's connector next to the flashing light". These displayed images provide additional information beyond that contained in the audio prompts. For example, these video images convey, in addition to that information conveyed by the audio and text, some idea about what "pads" and a "connector" look like, where and how the pads should be applied to the patient, and where the pads are connected to the defibrillator.

The images are stored in a conventional database capable of storing video information. The database may have entries containing bit-map files for display on the video display 40 as well as other information useful for sequencing the display, formatting the presentation and timing the display with the provision of audio instruction. Other formats may be used as well. Storage of images and arrangement of images in a database may be done according to any known technique.

Figure 5:
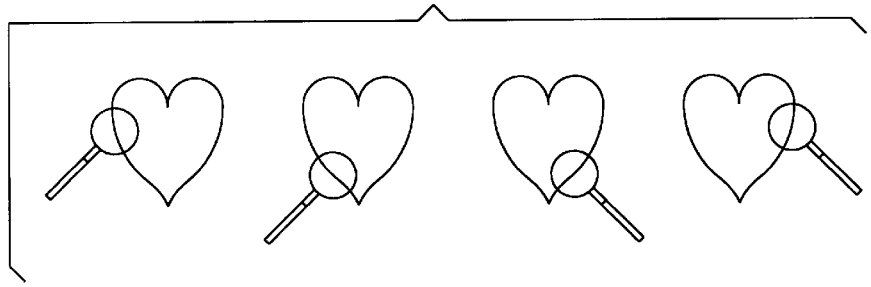
FIGS. 5–10 are additional sequences of images to be displayed by the audio/video output unit of FIG. 2.
Figure 6:
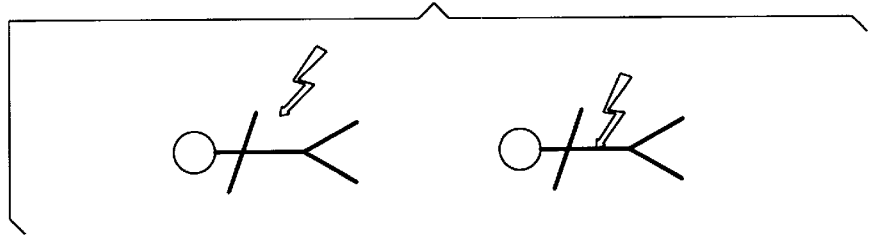
Figure 7:
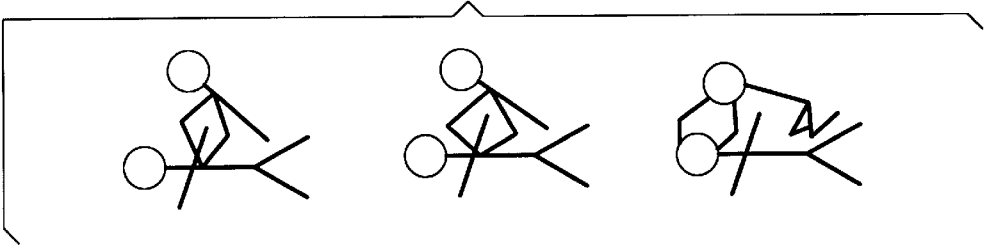
Figure 8:
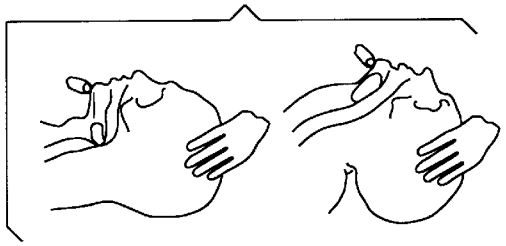
Figure 9:
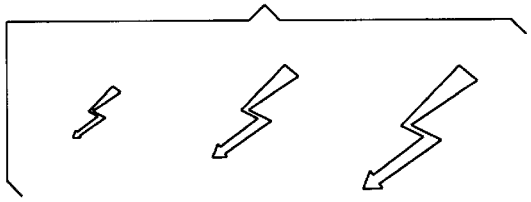
Figure 10:
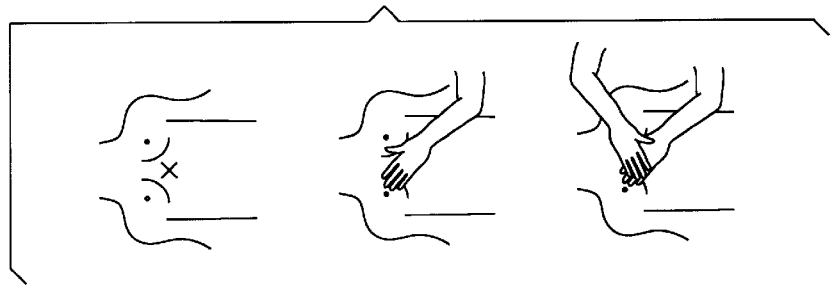

The defibrillator may be provided with additional image sequences, such as an image sequence to inform the operator that the defibrillator is analyzing the heart rhythm and that the operator should not touch the patient. This exemplary image sequence is shown in FIG. 5. FIG. 6 illustrates a sequence that could be used when a shock is delivered. FIG. 7 illustrates a sequence of images that could be used during CPR. FIG. 8 illustrates images that could be used to inform the operator of the proper way to tilt the patient's head to open the airway when beginning CPR. FIG. 9 illustrates a sequence of images that could be displayed to inform the operator that the defibrillator is charging and that the patient should be touched. FIG. 10 illustrates a sequence of images that could be displayed to instruct the operator on proper hand placement during CPR. Any other video image or sequence of images capable of being displayed on the display may also be used.

It should be understood that various changes and modifications of the embodiments shown in the drawings and described in the specification may be made within the spirit and scope of the present invention. Thus, for example, although the audio/video output unit is described as a single unit that provides both audio and video outputs, a separate audio unit and separate video unit could be used instead. Accordingly, it is intended that all matter contained in the above description and shown in the accompanying drawings be interpreted in an illustrative and not in a limiting sense. The invention is limited only as defined in the following claims and the equivalents thereto.

What is claimed is:

1. A defibrillator, comprising:
   circuitry configured to produce a defibrillatory shock; and
   an audio/video output unit, comprising:
   a database of video image information stored in a memory;
   a video display; and
   a video formulation unit coupled to the memory and configured to retrieve video information from the database of video image information and present corresponding information to the video display for display.

2. The defibrillator of claim 1, wherein the audio/video output unit further comprises an audio speaker configured to output audio information.

3. The defibrillator of claim 1, wherein the video formulation unit comprises a controller configured to receive signals indicative of a current operating state of the defibrillator, and wherein the video formulation unit is configured to retrieve video from the database of video information corresponding to the current operating state of the defibrillator.

4. The defibrillator of claim 1, further comprising an audio speaker, and wherein the video formulation unit is further configured to receive audio information from the database of video information and correlate the video information to be displayed with the received audio information to be output by the audio speaker.

5. The defibrillator of claim 1, further comprising an output generator configured to receive the video image information and determine a duration of images, a sequencing of images and repeat frequency of image sequences for display by the video display.

6. The defibrillator of claim 1, further comprising an instruction generator comprising a memory configured to contain instructions relating to operation of the audio/video output unit, said instruction generator being configured to receive signals indicative of the operating state of the defibrillator and to return at least one operational instruction derived from information contained in the memory.

7. The defibrillator of claim 1, wherein the video information includes still images.

8. The defibrillator of claim 1, wherein the video information includes animated images.

9. The defibrillator of claim 1, wherein the video information includes motion images.

10. The defibrillator of claim 1, wherein the video information contains a combination of textual information and at least one of still images, animated images and motion images.

11. The defibrillator of claim 1, wherein the database of video information contains bit map files corresponding to the video images to be displayed by the video display.

12. The defibrillator of claim 3, wherein the information includes at least one of user inputs, patient signals, and device inputs.

13. The defibrillator of claim 12, wherein the patient signals includes at least one of ECG data and instantaneous heart rate.

14. The defibrillator of claim 12, wherein the device inputs includes at least one of impedance data and internal voltage data.

15. A defibrillator, comprising:

circuitry configured to deliver a defibrillatory shock; and an audio/video output unit configured to receive inputs relating to a current operational state of the circuitry configured to deliver the defibrillatory shock, and provide audio and video instructions relating to operation of the defibrillator.

16. The defibrillator of claim 15, wherein the audio/video output unit is further configured to provide textual instructions relating to operation of the defibrillator.

17. A method of instructing an operator of a defibrillator during defibrillation of a victim of sudden cardiac arrest, comprising:

determining a current operating state of the defibrillator; and providing video instructions to the operator related to the current operating state of the defibrillator.

18. The method of claim 17, further comprising:

providing audio instructions to the operator related to the current operating state of the defibrillator.

19. The method of claim 17, further comprising:

providing textual instructions to the operator relating to the current operating state of the defibrillator.

20. The method of claim 17, wherein determining includes sensing at least one of user inputs, patient signals and device inputs.

* * * * *